US 6,613,581 B1

(12) United States Patent
Wada et al.

(10) Patent No.: US 6,613,581 B1
(45) Date of Patent: Sep. 2, 2003

(54) MICROFLUIDIC ANALYTIC DETECTION ASSAYS, DEVICES, AND INTEGRATED SYSTEMS

(75) Inventors: H. Garrett Wada, Atherton, CA (US); Matthew B. Murphy, San Francisco, CA (US)

(73) Assignee: Caliper Technologies Corp., Mountain View, CA (US)

(*) Notice: Subject to any disclaimer, the term of this patent is extended or adjusted under 35 U.S.C. 154(b) by 190 days.

(21) Appl. No.: 09/641,468

(22) Filed: Aug. 17, 2000

Related U.S. Application Data

(60) Provisional application No. 60/150,923, filed on Aug. 26, 1999.

(51) Int. Cl.$^7$ .............................................. G01N 33/543
(52) U.S. Cl. ..................... 436/518; 435/7.21; 435/6; 435/7.2; 436/514; 422/99; 422/68.1; 422/50; 210/222
(58) Field of Search ................. 435/7.21, 6, 7.2; 436/514; 210/222; 422/99, 68.1, 100, 50

(56) References Cited

U.S. PATENT DOCUMENTS

| | | | |
|---|---|---|---|
| 4,390,403 A | | 6/1983 | Batchelder |
| 4,827,131 A | * | 5/1989 | Moscovitch ............... 250/337 |
| 4,908,112 A | | 3/1990 | Pace |
| 5,126,022 A | | 6/1992 | Soane et al. |
| 5,498,392 A | | 3/1996 | Wilding et al. |
| 5,571,410 A | | 11/1996 | Swedberg et al. |
| 5,585,069 A | | 12/1996 | Zanzucchi et al. |
| 5,587,128 A | | 12/1996 | Wilding et al. |
| 5,593,838 A | | 1/1997 | Zanzucchi et al. |
| 5,603,351 A | | 2/1997 | Cherukuri et al. |
| 5,635,358 A | | 6/1997 | Wilding et al. |
| 5,637,469 A | * | 6/1997 | Wilding et al. ............ 435/7.21 |
| 5,699,157 A | | 12/1997 | Parce |
| 5,750,015 A | | 5/1998 | Soane et al. |
| 5,779,868 A | | 7/1998 | Parce et al. |

(List continued on next page.)

FOREIGN PATENT DOCUMENTS

| | | |
|---|---|---|
| WO | WO 96/04547 | 2/1996 |
| WO | WO 97/02357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/49548 | 11/1998 |

(List continued on next page.)

OTHER PUBLICATIONS

Cohen, C.B. et al., "A Microchip–Based Enzyme Assay for Protein Kinase A," *Anal. Chem.* (1999) 273:89–97.
Dasgupta, P.K. et al., "Electroosmosis: A Reliable Fluid Propulsion System for Flow Injection Analysis," *Anal. Chem.* (1994) 66:1792–1798.
Jacobson, S.C. et al., "Fused Quartz Substrates for Microchip Electrophoresis," *Anal. Chem.* (1995) 67:2059–2063.
Manz, A. et al., "Electroosmotic pumping and electrophoretic separations for miniaturized chemical analysis systems," *J. Micromech. mciroeng.* (1994) 4:257–265.

(List continued on next page.)

*Primary Examiner*—Long V. Le
*Assistant Examiner*—Deborah A Davis
(74) *Attorney, Agent, or Firm*—Quine Intellectual Property Law Group, P.C.; Matthew B. Murphy; Andrew L. Filler

(57) ABSTRACT

Methods of detecting a component of interest, such as a protein, in a microfluidic system are provided. The methods include the use of a component-binding moiety specific to the component of interest, such as an antibody, to detect the component of interest. Also included are microfluidic devices and integrated systems for performing such assays, including devices utilizing flowable or fixed particle sets.

32 Claims, 4 Drawing Sheets

U.S. PATENT DOCUMENTS

| | | |
|---|---|---|
| 5,800,690 A | 9/1998 | Chow et al. |
| 5,804,384 A * | 9/1998 | Muller et al. .................. 436/6 |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,942,443 A | 8/1999 | Parce et al. |
| 5,948,227 A | 9/1999 | Dubrow |
| 5,952,173 A * | 9/1999 | Hansmann et al. ............ 435/6 |
| 5,955,028 A | 9/1999 | Chow |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |
| 5,965,410 A | 10/1999 | Chow et al. |
| 5,972,187 A | 10/1999 | Parce et al. |
| 5,976,336 A | 11/1999 | Dubrow et al. |
| 5,989,402 A | 11/1999 | Chow et al. |
| 6,001,231 A | 12/1999 | Kopf-Sill |
| 6,004,515 A | 12/1999 | Parce et al. |
| 6,011,252 A | 1/2000 | Jensen |
| 6,012,902 A | 1/2000 | Parce |
| 6,042,710 A | 3/2000 | Dubrow |
| 6,046,056 A * | 4/2000 | Parce et al. ................. 436/514 |
| 6,068,752 A | 5/2000 | Dubrow et al. |
| 6,071,478 A | 6/2000 | Chow |
| 6,074,725 A | 6/2000 | Kennedy |
| 6,080,295 A | 6/2000 | Parce et al. |
| 6,280,618 B2 * | 8/2001 | Watkins et al. ............. 210/222 |

FOREIGN PATENT DOCUMENTS

| | | |
|---|---|---|
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 99/64848 | 12/1999 |
| WO | WO 00/09753 | 2/2000 |
| WO | WO 00/50172 | 8/2000 |
| WO | WO 00/50642 | 8/2000 |
| WO | WO 01/14064 | 3/2001 |

OTHER PUBLICATIONS

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

Sundberg, S. A., "High–throughput and ultra–high–throughput Screening: solution—and cell– based approaches," *Current Opinions in Biotechnology* 2000, 11:47–53.

* cited by examiner

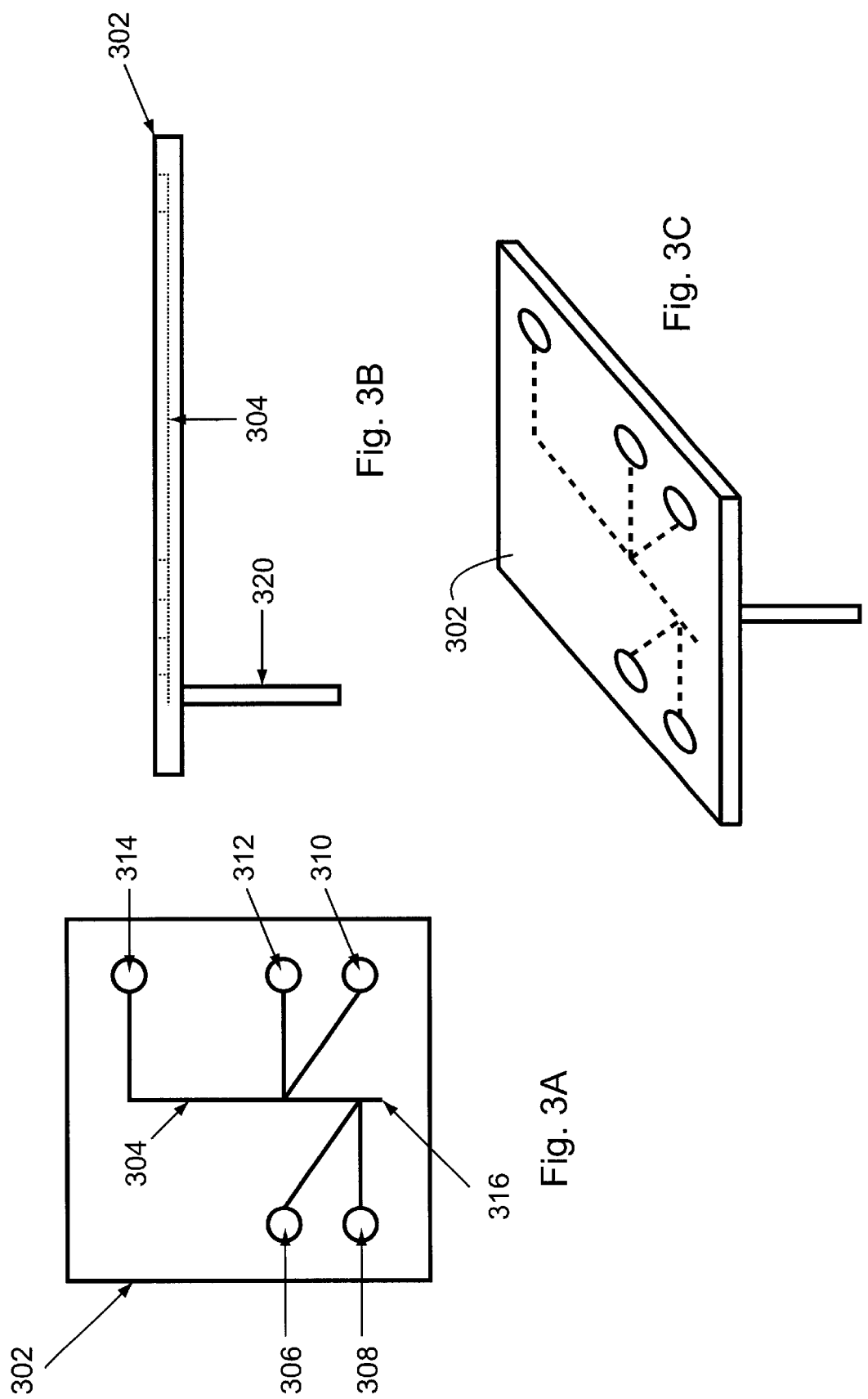

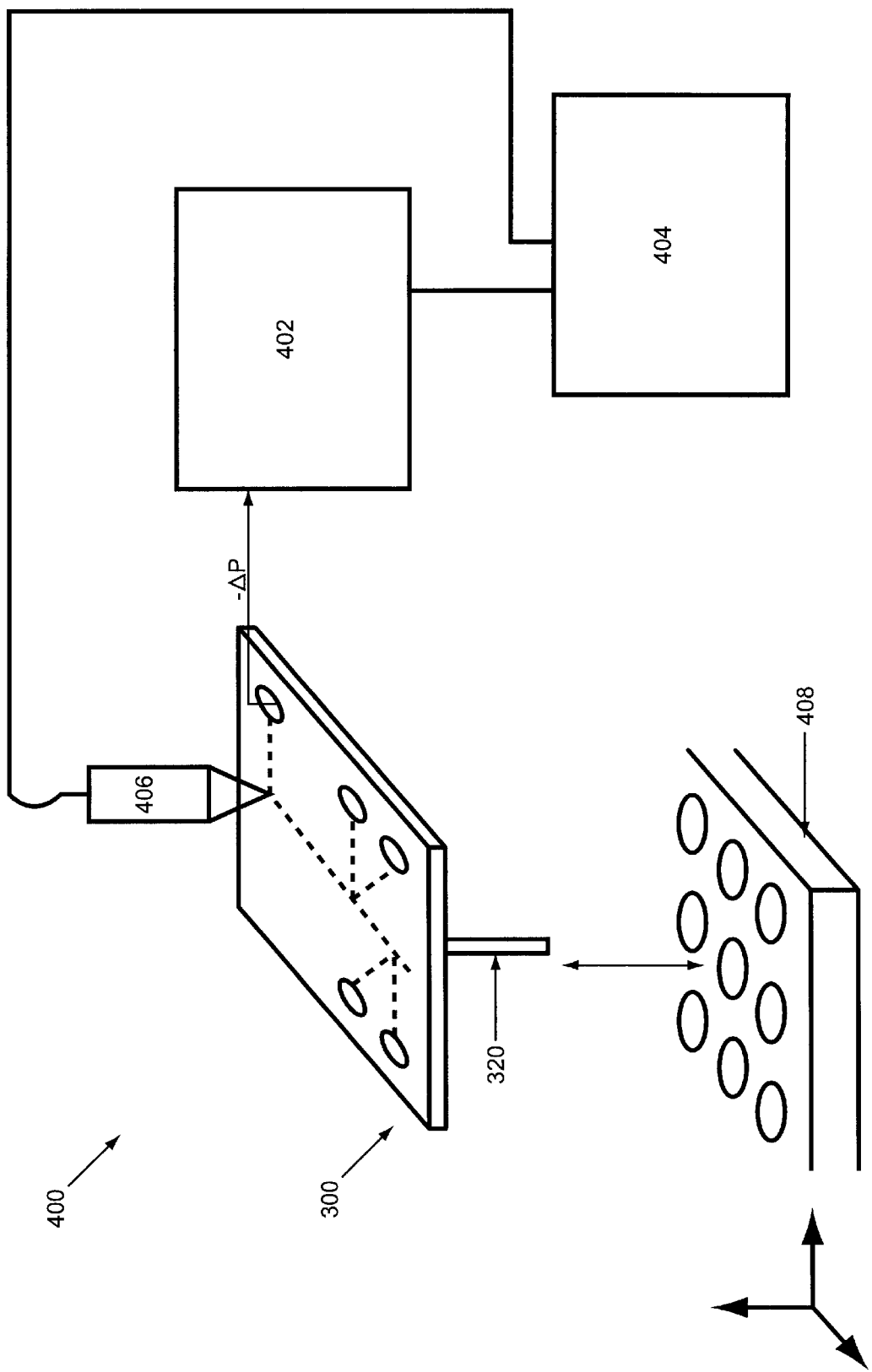

MICROFLUIDIC ANALYTIC DETECTION ASSAYS, DEVICES, AND INTEGRATED SYSTEMS

CROSS-REFERENCE TO RELATED APPLICATIONS

Pursuant to 35 U.S.C. §119(e) and any other applicable statute or rule, the present application claims benefit of and priority to U.S. Ser. No. 60/150,923, entitled "Microfluidic Analytic Detection Assays, Devices, and Integrated Systems," filed Aug. 26, 1999 by Wada and Murphy.

BACKGROUND OF THE INVENTION

Analytic detection of biomolecules, e.g., proteins, nucleic acids, and the like, is fundamental to molecular biology. In many applications, it is desirable to detect the presence of one or more particular molecules in a sample. For example, identification of a particular DNA sequence within a mixture of restriction fragments is used to determine the presence, position, and number of copies of a gene in the genome. It is also an integral technique in DNA typing. Analytic detection is also used, e.g., in disease diagnosis and drug development, to determine the presence of a particular antibody or protein, e.g., in a blood sample or large chemical library. Detection of biomolecules is therefore of fundamental value in, e.g., diagnostic medicine, archaeology, anthropology and modem criminal investigation. To meet these needs many techniques, e.g., DNA blotting, RNA blotting, protein blotting, and ELISA assays, have been developed to detect the presence of a particular molecule or fragment in the midst of a complex sample containing similar molecules.

For example, western blotting is useful for detecting one or more specific proteins in a complex protein mixture, such as a cell extract. The procedure involves fractionating the protein mixture, generally by denaturing polyacrylamide gel electrophoresis, and transferring and immobilizing the mixture onto a solid membrane of either nitrocellulose or nylon by electroblotting. The loaded membrane is then incubated with an antibody raised against the protein of interest. The antibody-antigen complex so formed on the membrane is then detected by a procedure that typically involves the application of a second antibody, raised against the first antibody, and to which an enzyme has been covalently linked. The insoluble reaction product generated by the enzyme action can then be used to indicate the position of the target protein on the membrane. The sensitivity of detection can be increased by amplification of the signal using either the biotin-streptavidin system or by chemiluminescence detection.

This classical procedure is very time consuming and labor intensive. For example, transferring the proteins to a membrane is generally a time consuming step and is typically done by capillary blotting or by the faster and more efficient methods of vacuum blotting or electrophoretic blotting.

More recently, new and faster microfluidic methods of performing biological assays in microfluidic systems have been developed, such as those described by the pioneering applications of Parce et al., "High Throughput Screening Assay Systems in Microscale Fluidic Devices" WO 98/00231 and in Knapp et al., "Closed Loop Biochemical Analyzers" (WO 98/45481; PCT/US98/06723). For example, high throughput methods for analyzing biological reagents, including proteins, are described in these applications.

Improved methods for performing western blot and affinity assays are, accordingly desirable, particularly those which take advantage of high-throughput, low cost microfluidic systems. The present invention provides these and other features by providing high throughput microscale systems for analyte detection, western blots, and the like, and many other features that will be apparent upon complete review of the following disclosure.

SUMMARY OF THE INVENTION

The present invention provides methods, devices, systems, and kits for detecting a component of interest in a complex mixture. Typically, the method comprises separating a mixture of components, which mixture of components contains the component of interest. To detect the component of interest, the mixture of components or the separated components are contacted with a component-binding moiety specific to the component of interest. The component-binding moiety binds to the component of interest and is detected, thereby detecting the component of interest.

In one embodiment, the component of interest and the various components of the mixture are labeled with two detectably different labels so that both the component of interest and the mixture of components are concurrently detected.

In another embodiment, the separated components are bound to or adsorbed to a particle set. The particle set is optionally stacked in a detection region and a component-binding moiety specific to the component of interest is directed into the region of the device containing the particle set with the bound components. The component-binding moiety thereby binds to the component of interest, thus providing detection of the component of interest.

The devices, systems, and methods of the invention are useful in a variety of detection systems, e.g., western assays, biotin-avidin systems, lectin/carbohydrate systems, and in other applications that will be apparent upon further review.

In one aspect, the method comprises providing a body structure having a plurality of microscale channels disposed therein, the plurality comprising a microfluidic separation channel and at least one side channel intersecting the separation channel, wherein the separation channel and the side channel are fluidly coupled. A mixture of components is flowed through the separation channel, resulting in separated components. A labeled component-binding moiety is then flowed through a side channel and into the separation channel, wherein it binds to the component of interest. The component-binding moiety is then detected, thereby detecting the component of interest.

The separated components are typically labeled components that are optionally detected simultaneously with the component-binding moiety. This embodiment optionally includes deconvoluting the detection signal to identify the separated components and the component of interest. This embodiment includes two detectably different label moieties having detectably different spectral characteristics, such as different excitation or emission maximum. The different labels include, but are not limited to fluorescent labels, chemiluminescent labels and colorimetric labels. For example, the separated components are optionally labeled with a first fluorescent dye and the component-binding moiety is labeled with a second fluorescent dye. These two dyes are typically detectably different. In another embodiment, the component of interest and the component-binding moiety are optionally labeled with detectably different colorimetric labels. In another embodiment, the component of interest is labeled with one type of label, e.g., chemiluminescent, and the component-binding moiety is labeled with a second type of label, e.g., fluorescent.

In another aspect, a microfluidic system comprising a particle set is provided. A body structure having at least one microfluidic channel disposed therein is provided, and a mixture of components is flowed through the microfluidic channel, separating the mixture of components and producing separated components. The separated components are then bound to a particle set comprising a plurality of particle member types. The separated components bound to the particle set are then contacted with a component-binding moiety specific to the component of interest, thereby binding the moiety to the component of interest. The component-binding moiety is then detected, thus detecting the component of interest. After being bound to the separated components, the particle set is flowed into a detection channel downstream of the separation and binding events. The particle set is optionally stacked or fixed in the detection channel. In one embodiment, stacking occurs against a barrier located in the detection channel.

The particle set is comprised of a plurality of particle member types, that optionally comprise a polymeric material, a silica material, a ceramic-material, a glass material, a magnetic material, a metallic material, an organic material, or a combination of these materials. In one embodiment, binding comprises adsorbing the separated components onto the members of the particle set. In these embodiments, the particle member types optionally comprise PVDF, nitrocellulose, or a polyamide, such as nylon and the like.

In other embodiments, the particle set is contacted with a blocking solution after binding the separated components to the particle set and prior to contacting the particle set with the component-binding moiety, thereby binding blocking moieties to open sites on the particle set. The blocking moiety is optionally a blocking protein or buffer containing casein, solubilized non-fat dry milk, gelatin, or bovine serum albumin.

The particle set with the bound component of interest is typically incubated with the component-binding moiety for a time ranging from about 10 seconds to about 30 minutes.

In some embodiments, the method comprises washing the particle set or the bound complexes comprising a component-of interest and a component-binding moiety prior to detection, thereby substantially removing component-binding moieties that are not bound to the component of interest.

The component of interest in the above methods is optionally a protein, a carbohydrate, biotin, avidin, or the like. The component-binding moiety is optionally a protein-binding moiety such as an antibody or a carbohydrate-binding moiety, such as a lectin. The antibody or other binding moiety is preferably specific to the protein or other component of interest. In other embodiments, the component of interest optionally comprises biotin and the component binding moiety is avidin or the component of interest comprises avidin and the binding moiety is biotin.

The mixtures of components of the invention are separated in one embodiment by electrophoresis in a polymer or gel, such as a polyacrylamide solution, matrix, or gel. In some embodiments, the mixture of components is separated and concurrently bound to the particle set and in others the mixture is separated and contacted with the particle set after separation. In this case, separation is performed in a separation matrix and binding of the separated components to the particle occurs downstream of the separation matrix. In alternate embodiments, the components are contacted by the component-binding moiety during the separation or just after and then directed into a detection region where they are simultaneously detected. In this embodiment, the components are separated on the basis of molecular weight, which is then determined by the retention time. The separated components are optionally labeled with a fluorescent dye and detected upon elution from the separation channel.

Detection optionally comprises optically detecting a chemiluminescent, calorimetric, or fluorescent label moiety that has been fixed to the component-binding moiety. The detection channel is typically located within the at least one microfluidic channel or intersecting the at least one microfluidic channel; and, optionally comprises a stacked particle set proximal to a detector.

In other embodiments, the body structure comprises a detection channel fluidly coupled to the separation channel and the side channel. In these embodiments, the mixture of components is separated by flowing the mixture through a separation matrix located in the separation channel; wherein the component-binding moiety is flowed into the separation channel downstream of the separation matrix and upstream of a detection point proximal to the detection channel. The side channel in some embodiments is proximal to the detection region.

In another embodiment, the mixture of components is flowed through the separation channel concurrently with flowing the component-binding moiety into the separation channel. The component-binding moiety is flowed in the same direction or the opposite direction as the mixture of components. In some embodiments, the component-binding moiety has an electrokinetic mobility opposite to that of the mixture of components.

In other embodiments, the method further comprises washing the side channel and separation channel, thereby substantially removing component-binding moieties that are not bound to the component of interest. Furthermore, the signal from the labeled component-binding moiety bound to the component of interest is typically detectable above a background level.

In another aspect, the invention also provides microfluidic devices for detecting the components of interest. In one embodiment, a microfluidic device for detecting a component of interest is provided. The device comprises a plurality of fluidly coupled microscale channels disposed therein. The plurality of channels typically comprises a first channel, a second channel, a third channel, a binding region, a detection region, a stacking region and a particle set. The first channel comprises a component separation region in which a mixture of components is separated. The second channel intersects the first channel and comprises a particle set disposed therein, which particle set comprises a plurality of particle member types. The third channel, which comprises a blocking solution and a labeled component-binding moiety specific to the component of interest, intersects the first channel. The binding region is fluidly coupled to the first channel, for binding the mixture of components to the particle set. The detection region is fluidly coupled to the first channel; and, the stacking region is positioned within the detection channel.

A second embodiment of the device is also provided. This device is also used in detecting a component of interest but does not include a particle set. The device comprises a plurality of fluidly coupled microscale channels disposed therein. The plurality of channels comprises a main channel, a side channel, and a detection region. The main channel comprises a component separation region in which a mixture of components is separated. The side channel, which intersects the main channel, comprises a component-binding moiety, and the detection region is fluidly coupled to the main channel.

The particle sets and separation channels for the devices are typically the same as those discussed above. In addition, these devices are incorporated into integrated systems. The integrated systems comprise one of the microfluidic devices as described above as well as a fluid direction system, and a detection system.

A fluid direction system is fluidly coupled to the microfluidic device and transports the sample or components through the microscale channels. The sample and components useful in the integrated systems of the invention are the same components useful in the above-described methods. The fluid direction system in some embodiments is an electrokinetic based fluid direction system or in other embodiments, a pressure based system.

The detection system is positioned proximal to the detection region or detection channel and detects one or more of the component-binding-moiety, the separated components and the component of interest. The detection system comprises a detector that is optionally one of the following: a chemiluminescent detector, a fluorescent detector or a calorimetric detector.

The control system is operably linked to the fluid direction system and instructs the fluid direction system to deliver or transport the sample and/or components through the microfluidic channels. The control system in some embodiments comprises a computer and software.

The computer is operably linked to the integrated system and includes software. The software analyzes and deconvolutes signals produced from detection and directs fluid movement in the system. The software directs movement of one or more of the following: movement of a sample through the component separation region or channel, resulting in separated components; movement of a particle set and the separated components to a binding region, resulting in binding of the separated components to the plurality of particle member types; movement of the component-binding moiety to the binding region, resulting in binding of the component-binding moiety to the component of interest; and, movement of the particle set, separated components, and the component-binding moiety to the detection region, where the component-binding moiety is detected, thereby detecting the component of interest. In addition the software directs movement of the one or more of the following through the separation channel or binding region: a buffer solution, a blocking solution, and a washing solution. It also operates to direct the particle set to a stacking region in some embodiments.

BRIEF DESCRIPTION OF THE DRAWING

FIG. 3A is a top view of an embodiment of a microfluidic device according to the teachings of the present invention including a body structure, microfabricated elements, and a pipettor channel;

FIG. 3B is a side view of the device of FIG. 3A;

FIG. 3C is a perspective view of the device of FIG. 3A.

FIG. 4: Schematic drawing of an integrated system of the invention further depicting incorporation of a microwell plate, a computer, detector and a fluid direction system.

Figure 1:
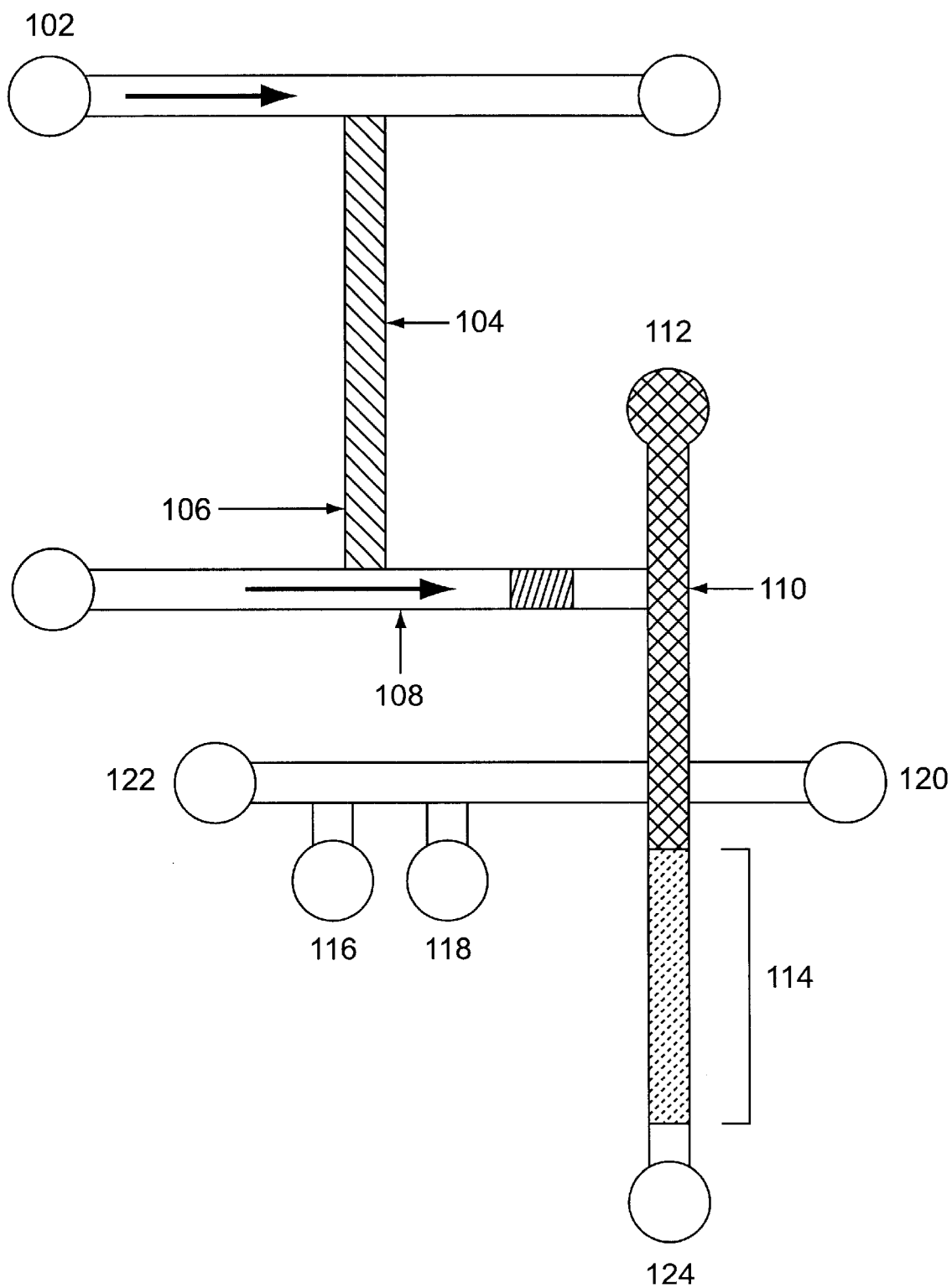
FIG. 1: Schematic drawing of the microfluidic elements of a device or system of the invention.
Figure 2:
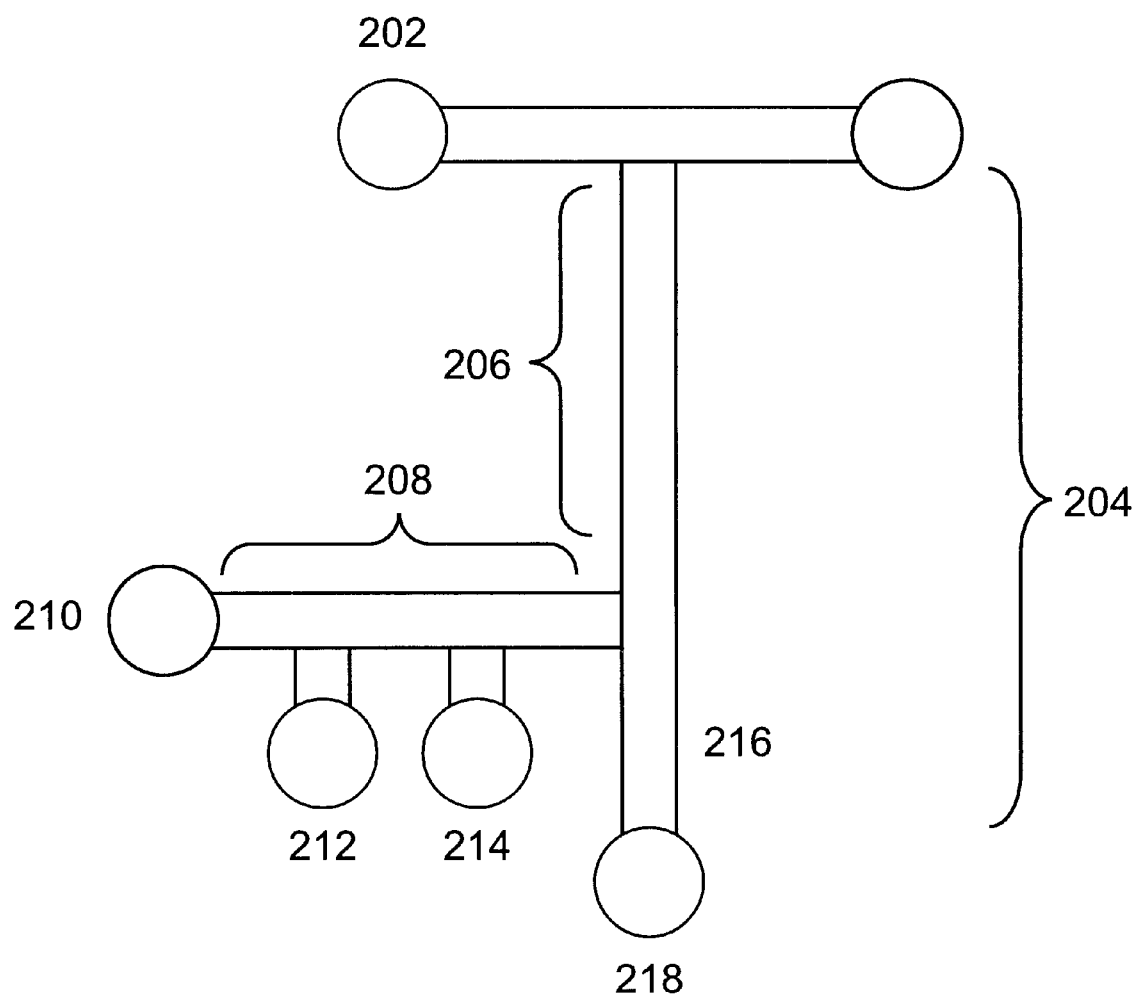
FIG. 2: Schematic drawing of the microfluidic elements of a device or system of the invention.

The integrated system is optionally used with either the device or body structure of FIG. 1 or FIG. 2 or FIG. 3.

DETAILED DISCUSSION OF THE INVENTION

The present invention provides new technology for detecting a component of interest in a complex mixture. For example, the new technology optionally replaces the standard western blot. Standard western blotting technology involves separation of a mixture of components and then a time-consuming blotting procedure to detect the protein of interest from the mixture. The present invention provides methods and microscale devices for continuous flow separation and detection. A time-consuming blotting step is not required, thus providing dramatically increased throughput as compared with prior art methods.

The present methods provide for separation of a mixture of components in a microfluidic separation channel or region. During or after separation, the component of interest is contacted by a moiety that specifically binds the component of interest. For example the component of interest is optionally a protein that is detected by a binding reaction with an antibody specific to the protein. The component of interest is detected after it binds to the moiety, which is typically a labeled moiety. When the component-binding moiety and the mixture of components are labeled with two detectably different labels, the present invention optionally detects both.

The component of interest is detected in the present invention by binding the component of interest to a binding moiety that is specific to the component of interest. The component of interest is optionally a protein, nucleic acid, carbohydrate, or the like. For example, the component of interest can optionally include biotin or avidin. The component is typically included in a complex mixture of various components, e.g., other proteins, nucleic acids, and the like. For example, the component of interest is optionally a component of a cell extract or serum sample.

In a preferred embodiment, such as in an assay analogous to a western assay or a western style assay, the component of interest is a protein. A "protein," as used herein, refers to a polymer of amino acid residues. The term applies to amino acid polymers in which one or more amino acid residue is an analog or mimetic of a corresponding naturally occurring amino acid, as well as to naturally occurring amino acid polymers. A protein of biological or other interest is optionally detected using the methods, devices, and systems of the present invention.

For example, a "western" analysis (this term is used herein to refer to antibody-protein binding analysis) is used to detect a specific protein of interest in a complex mixture of components, such as a cell extract. The procedure involves fractionating the protein mixture by electrophoresis and binding the protein of interest to an antibody specific to that protein. The methods of the present invention are applicable to other analytic detection assays as well, e.g., detection of nucleic acids or carbohydrates. For example, a carbohydrate of interest is optionally detected using the methods, devices, and systems of the present invention by providing a lectin as the component-binding moiety to bind the carbohydrate of interest.

In one embodiment of the present invention, the mixture of proteins is separated in a microfluidic separation channel, and then adsorbed onto a particle set. The solid support particle set, with proteins attached, is then stacked in a detection channel according to molecular weight. The particle set is then optionally contacted with a variety of solutions, e.g., a buffer, a blocking solution, or a washing solution. An antibody specific to the protein of interest is added to the stacking region to bind to the protein of interest. The antibody, which is labeled, is then detected.

In another embodiment of the invention, a complex mixture of components, e.g., proteins, is separated, e.g., by electrophoresis, in a separation channel of the microfluidic device and then contacted with a labeled component-binding moiety, such as an antibody specific to the component of interest, providing bound complexes comprising the component of interest and the component-binding moiety. In one aspect, the mixture of proteins is labeled with one label and the component-binding moiety is labeled with a different label such that they are simultaneously detected using the two different labels.

In addition, the present invention provides microfluidic devices and systems for use in detecting a component of interest by the above methods. These systems and methods are described below.

I. The Microfluidic System

The microfluidic device of the present invention is used to detect the presence of a particular component of interest, e.g., a protein of interest. The device generally comprises a body structure with microscale channels fabricated therein. For example, the present system comprises, e.g., a separation channel, a binding channel, and a side channel. The channels are fluidly coupled to each other and to various reservoirs or other sources of materials. Materials used in the present invention include but are not limited to buffers, blocking solutions, washing solutions, a sample comprising a mixture of proteins, and a particle set. In addition, the channels optionally comprise various regions, such as a detection region or a stacking region.

For example, various channels and channel regions are disposed throughout the microfluidic device. The devices typically.include a separation channel for separating a sample mixture into its various components. For example, a mixture of proteins as it flows through the separation channel or separation region will be separated into separated proteins. Preferably, the separation channel is a gel filled channel, e.g., a linear polyacrylamide gel filled channel or a polymer solution filled channel, e.g., a polyacrylamide polymer solution, that separates the various components based on molecular weight, wherein each component is eluted from the separation channel with a different retention time. In this embodiment, the components are then optionally detected and their molecular weights determined by the retention time.

A binding channel is also optionally included in the microfluidic devices and systems in the present invention. The binding channel or binding region is typically downstream of the separation channel. The term "downstream" refers to a location in a channel or microfluidic device that is farther along the channel or plurality of channels in a selected direction of fluid or material flow, relative to a selected site or region. For example, the binding region is optionally farther along in the direction of flow in the channel system than the separation channel; therefore, the fluid flows through the separation channel first and then into the binding region or channel. A binding region or channel is preferred when the method of the invention uses a particle set for adsorbing or attaching the separated components. In that case, the separated components are incubated with a particle set for a period of time that allows adsorption or binding of the components to the particle member types to take place.

Other features of the present devices are optionally upstream from the binding channel. For example, a reservoir for a binding buffer or the sample well is optionally upstream from the binding buffer well. The reservoirs are the locations or wells at which samples, components, reagents and the like are added into the device for assays to take place. Introduction of these elements into the system is carried out as described below. The reservoirs are typically placed so that the sample or reagent is added into the system upstream from the location at which it is used. "Upstream" refers to a location in a channel or system of channels that is farther along the channel or plurality of channels in a direction that is opposite the flow of fluid or material flow, relative to a selected site or region.

Detection regions are also included in the present devices. The detection region is optionally a subunit of a channel, or it optionally comprises a distinct channel that is fluidly coupled to the plurality of channels in the microfluidic device. The detection region is optionally located at the elution point of the separation channel or region. For example, the detection region located at the most downstream point or end of the separation channel detects the separated components as they are eluted from the separation region or channel. In other embodiments, the detection region is optionally located at the downstream end of the device just upstream from a waste well. A detection region is optionally located at whatever point in the device that detection of the components is desired. For example, at the end of the binding region after the component-binding moiety has been added, the component-binding moiety is optionally detected.

The detection window or region at which a signal is monitored typically includes a transparent cover allowing visual or optical observation and detection of the assay results, e.g., observation of a colorimetric or fluorometric signal or label. Examples of suitable detectors are well known to those of skill in the art and are discussed in more detail below.

The detection region optionally comprises a stacking region. The stacking region provides a particle retention or capture region for fixing in place the particle set, which is optionally fixed in place or mobile. The particle retention region or stacking region optionally includes a region of increased or decreased microchannel depth or width or other physical barrier (e.g., a groove, mesh, net, matrix, etc.), an electromagnetic field or porous matrix (e.g., sieving matrices), or other means of inhibiting particle movement in or adjacent to the stacking region. For more discussion of particle retention regions, see, U.S. Ser. No. 60/128,643 filed Apr. 4, 1999, entitled "Manipulation of Microparticles In Microfluidic Systems," by Burd Mehta et al. and U.S. Ser. No. 09/510,626, of the same title, filed Feb. 22, 2000 by Burd Mehta et al.

One embodiment of the present system is illustrated in FIG. 1. As shown, the system comprises protein sample well 102, which is used to introduce a sample comprising a mixture of components into the system. From protein sample well 102, a sample is then directed into separation channel 104, where a mixture of components, e.g., of proteins, is separated, e.g., by electrophoresis. Detector 106 is positioned proximal to separation channel 104 to detect the components as they elute from separation channel 104 into elution region 108. Upon flowing into elution region 108, a binding buffer is added, which binding buffer is optimized to facilitate attachment of the separated proteins to the particle set in binding channel 110. After leaving separation channel 104 in the binding buffer, the components are then directed into binding channel 110. In binding channel 110, the components are mixed with a particle set from particle well 112. The particle set is released from particle well 112 into binding channel 110. The particle set with the components attached or adsorbed onto the particle member types is then directed to detection region 114, where the particle member types of the particle set are optionally stacked. While the beads are stacked in detection region 114, e.g., stacked against a porous barrier or against a shallower depth channel region, various solutions are directed into detection region 114 for reaction with the particle member types of the particle set and the components. Various reservoirs, 116, 118, 120, and 122, of materials are fluidly coupled to detection region 114 for delivery of, e.g., washing solution, blocking solution, antibody-enzyme conjugate, and detection substrate. When the assay and detection are complete, the sample components are optionally directed to waste well 124 for disposal or retrieval.

Another embodiment is illustrated in FIG. 2. The plurality of channels comprise a main channel and a side channel as described below. A sample is optionally introduced into the device through sample well 202 and is transported into main channel 204. Main channel 204 comprises separation region 206 and detection region 216. A sample is transported through separation region 206, where the sample is separated into its individual components. The components are then contacted with a component-binding moiety that binds specifically to the component of interest in the sample. The component-binding moiety is optionally transported from component-binding moiety well 210 through side channel 208 to contact the separated components as they exit separation region 206 and flow into detection region 216. Alternatively the component-binding moiety is flowed from well 210 and then flowed upstream through separation region 206 to contact the separated components as they are being separated on the separation matrix located in separation region 206. For example, in an electrophoretic separation, a derivatized component-binding moiety, e.g., an acetylated antibody, flows in the opposite direction as the components of interest in the electrophoretic separation matrix. Side channel 208, which is optionally used to introduce the component-binding moiety or the derivatized component-binding moiety, is typically located proximal to detection region 216. Preferably, side channel 208 is between about 0.5 mm and about 2.5 mm upstream from detection region 216. For example side channel 208 is optionally 1.0 mm upstream from detection region 216. Side channel 208 is also optionally used to introduce buffers and washing solutions into main channel 204. Buffer well 212 and washing solution well 214 serve as sources for buffers and washing solutions to be introduced into the device. When the assay of interest is complete and the component(s) of interest has been detected, the components are then optionally directed into waste well 218 for disposal or retrieval.

A variety of microscale systems are optionally adapted to the present invention by incorporating separations gels, particle sets, antibodies, blocking solutions, and the like. Microfluidic devices which can be adapted to the present invention by the addition of western assay components are described in various PCT applications and issued U.S. Patents by the inventors and their coworkers, including U.S. Patent No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, and U.S. Pat. No. 5,842,787 (Anne R. Kopf-Sill et al.) issued Dec. 1, 1998; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548.

For example, pioneering technology providing cell based microscale assays are set forth in Parce et al. "High Throughput Screening Assay Systems in Microscale Fluidic Devices" WO 98/00231 and, e.g., in U.S. Ser. No. 60/128,643 filed Apr. 4, 1999, entitled "Manipulation of Microparticles In Microfluidic Systems," by Mehta et al. Complete integrated systems with fluid handling, signal detection, sample storage and sample accessing are available. For example, Parce et al. "High Throughput Screening Assay Systems in Microscale Fluidic Devices" WO 98/00231 provide pioneering technology for the integration of microfluidics and sample selection and manipulation.

In general, cells, modulators and other components can be flowed in a microscale system by electrokinetic (including either electroosmotic or electrophoretic) techniques, or using pressure-based flow mechanisms, or combinations thereof.

One method of achieving transport or movement of transmitters, transport modulators, and even cells (particularly transmitters and modulators) through microfluidic channels is by electrokinetic material transport. "Electrokinetic material transport systems," as used herein, include systems that transport and direct materials within a microchannel and/or chamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of transmitters, cells, modulators, etc. suspended within the fluid. Similarly, the components, e.g., proteins, antibodies, carbohydrates, etc. can be charged, in which case they will move toward an oppositely charged electrode (indeed, in this case, it is possible to achieve fluid flow in one direction while achieving particle flow in the opposite direction). In this embodiment, the fluid can be immobile or flowing and can comprise a matrix as in electrophoresis.

In general, electrokinetic material transport and direction systems also include those systems that rely upon the electrophoretic mobility of charged species within the electric field applied to the structure. Such systems are more particularly referred to as electrophoretic material transport systems. For example, in the present system separation of a mixture of components into its individual components optionally occurs by electrophoretic separation. In addition, a component may be transported through the channels in a direction opposite that of the mixture of components or separated components by electrophoretic transport. For example, the component-binding moiety optionally comprises a label or functional group that provides it an electrokinetic mobility opposite to the mixture of components and therefore it is optionally flowed in the opposite direction of the mixture of components. For example, an antibody is optionally derivatized, e.g., an acetylated antibody, to flow counter to the proteins or other components in the separation region so that the antibody does not contribute any background label in the detection region. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material which alters the surface charge of the channel.

A variety of electrokinetic controllers and systems are described, e.g., in Ramsey WO 96/04547, Parce et al. WO 98/46438 and Dubrow et al., WO 98/49548, as well as a variety of other references noted herein.

Use of electrokinetic transport to control material movement in interconnected channel structures was described, e.g., in WO 96/04547 and U.S. Pat. No. 5,858,195 to Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled components in one or more channels toward a waste reservoir. Particularly, modulation of the voltages applied at the various reservoirs can move and direct fluid flow through the interconnected channel structure of the device.

Other methods of transport are also available. For example, cells are desirably flowed using pressure-based flow mechanisms. Pressure forces can be applied to microscale elements to achieve fluid movement using any of a variety of techniques. Fluid flow (and flow of materials suspended or solubilized within the fluid, including cells or other particles) is optionally regulated by pressure based mechanisms such as those based upon fluid displacement, e.g., using a piston, pressure diaphragm, vacuum pump, probe or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit, or is a combination of such forces.

In other embodiments, a vacuum source is applied to a reservoir or well at one end of a channel to draw the suspension through the channel. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Hydrostatic, wicking and capillary forces are also optionally used to provide pressure for fluid flow of materials such as cells or protein mixtures. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

Mechanisms for reducing adsorption of materials during fluid-based flow are described in "PREVENTION OF SURFACE ADSORPTION IN MICROCHANNELS BY APPLICATION OF ELECTRIC CURRENT DURING PRESSURE-INDUCED FLOW" filed May 11, 1999 by Parce et al., Attorney Docket Number 01-78-0. In brief, adsorption of cells, components, proteins, antibodies, and other materials to channel walls or other microscale components during pressure-based flow can be reduced by applying an electric field such as an alternating current to the material during flow.

Mechanisms for focusing cells and other components into the center of microscale flow paths, which is useful in increasing assay throughput by regularizing flow velocity, e.g., in pressure based flow, is described in "FOCUSING OF MICROPARTICLES IN MICROFLUIDIC SYSTEMS" by H. Garrett Wada et al. Ser. No. 60/134,472, filed May 17, 1999. In brief, cells are focused into the center of a channel by forcing fluid flow from opposing side channels into the main channel comprising the cells, or by other fluid manipulations. Diffusible materials such as the components of the present invention are also optionally washed from cells as described by Wada et al. during flow of the cells, i.e., by sequentially flowing buffer into a channel in which cells are flowed and flowing the buffer back out of the channel.

In an alternate embodiment, microfluidic systems can be incorporated into centrifuge rotor devices, which are spun in a centrifuge. Fluids and particles travel through the device due to gravitational and centripetal/centrifugal pressure forces.

In addition to transport through the microfluidic system, the invention also provides for introduction of the sample or mixture of components to be assayed, e.g., for a protein of interest, into the microfluidic system.

Sources of Assay Components and Integration With Microfluidic Formats

Reservoirs or Wells are Provided in the Present Invention as Sources of Buffers, blocking solutions, washing solutions, and the like. Such wells include, e.g., protein sample well 102, particle well 112, washing solution well 112, and buffer well 212. Additional reservoirs are optionally present for the sample or mixture of components to be tested for the component of interest and for a particle set to be used in binding a mixture of components.

Sources of samples, mixtures of components, and reagents, e.g., washing solutions, blocking solutions, and the like, are fluidly coupled to the microchannels noted herein in any of a variety of ways. In particular, those systems comprising sources of materials set forth in Knapp et al. "Closed Loop Biochemical Analyzers" (WO 98/45481; PCT/US98/06723) and Parce et al. "High Throughput Screening Assay Systems in Microscale Fluidic Devices" WO 98/00231 and, e.g., in U.S. Ser. No. 60/128,643 filed Apr. 4, 1999, entitled "Manipulation of Microparticles In Microfluidic Systems," by Mehta et al. are applicable.

In these systems, a "pipettor channel" (a channel in which components can be moved from a source to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale device itself and others.

For example, the source of a cell type, component, or buffer can be a microwell plate external to the body structure, having, e.g., at least one well with the selected cell type or component. Alternatively, a well disposed on the surface of the body structure comprising the selected cell type, component, or reagent, a reservoir disposed within the body structure comprising the selected cell type, component, mixture of components, or reagent; a container external to the body structure comprising at least one compartment comprising the selected particle type, component, or reagent, or a solid phase structure comprising the selected cell type or reagent in lyophilized or otherwise dried form.

A loading channel region is optionally fluidly coupled to a pipettor channel with a port external to the body structure. The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like.

The integrated microfluidic system of the invention optionally includes a very wide variety of storage elements for storing reagents to be assessed. These include well plates, matrices, membranes and the like. The reagents are stored in liquids (e.g., in a well on a microtiter plate), or in lyophilized form (e.g., dried on a membrane or in a porous matrix), and can be transported to an array component, region, or channel of the microfluidic device using conventional robotics, or using an electropipettor or pressure pipettor channel fluidly coupled to a region or channel of the microfluidic system.

Another type of reagent optionally included in or introduced into the above devices is a particle set, made from particle member types. The particle set is used for binding or adsorbing the separated components and stacking them into the detection region according to retention or elution time from the separation matrix. This allows the identification of the component of interest when it binds to a labeled component-binding moiety.

The particle member types typically comprise one of the following: a polymeric material, a silica material, a ceramic material, a glass material, a magnetic material, a metallic material, an organic material, or the like. For example, the particles optionally comprise polymer or ceramic beads. Preferably, the particle member types or beads comprise PVDF, nitrocellulose, or polyamide, e.g., nylon.

The particle member types are optionally stored in a well or reservoir, such as particle well 112, and released into the device or system as needed or contained within the device in region or channel in which they will be used. For example, particles are optionally released from particle well 112 into binding channels 110 or stacked in detection region 114. The particles may be stored and introduced as described above. Additional information on storage, placement and usage of particle sets in microfluidic devices is found, e.g., in U.S. patent application Ser. No. 60/128,643, filed Apr. 9, 1999 by Mehta et al.

In general, the mixture of compounds is separately introduced into the assay systems described herein, or at least introduced in relatively manageable pools of sample materials. The mixture is then separated into its various components, e.g., proteins. The separated components are optionally mixed with a particle set and/or a component-binding moiety, e.g., an antibody, and detected due to a specific binding reaction with the component-binding moiety.

The above devices, systems, features, and components are used in the methods described below to detect a component of interest, e.g., a protein, carbohydrate or the like.

II. Separation of Components

The samples or mixtures of components in the present invention are separated in a separation region or separation channel of the microfluidic devices. A "mixture of components," as used herein, refers to a combination, known or unknown, of biological components, e.g., proteins, carbohydrates, or nucleic acids. The components can be in a complex mixture, such as blood, serum, cell extracts, or in a purified solution, such as a buffered solution of proteins.

Upon introduction of the sample into the microfluidic device the sample is typically separated into its individual components. This separation is performed in a separation region or channel, such as separation channel 104 or separation region 206, as described above and shown in FIGS. 1 and 2. The separation channel or region typically comprises a separation matrix. When the sample is flowed through the separation matrix, the components are separated, e.g., based on a physical or chemical properties, such as molecular weight or charge. The separation matrix optionally comprises a polymer, a gel, or a solution.

Electrophoretic separation is the separation of substances achieved by applying an electric field to samples in a solution or gel. In its simplest form, it depends on the different velocities with which the substances or components move in the field. The velocities depend, e.g., on the charge and size of the substances.

Preferably, the channel, such as separation channel 104, is polyacrylamide gel, linear polyacrylamide, filled channel on which the mixture of components is electrophoretically separated based on charge/mass ratio or molecular weight. If the components are detected as they exit the separation region, the components are optionally identified by their retention times.

Other gel electrophoretic media that are optionally placed in a separation channel or region of the invention include silica gels such as Davisil Silica, E. Merck Silica Gel, Sigma-Aldrich Silica Gel (al available from Supelco) in addition to a wide range of silica gels available for various purposes as described in the Aldrich catalogue/handbook (Aldrich Chemical Company, Milwaukee, Wis.). Preferred gel materials include agarose based gels, various forms of acrylamide based gels (reagents available from, e.g., Supelco, SIGMA, Aldrich, Sigma-Aldrich and many other sources), colloidal solutions, such as protein colloids (gelatins) and hydrated starches. For a review of electrophoretic separation techniques and polyacrylamide gels, see, e.g., The Encyclopedia of Molecular Biology, Kendrew (ed.) (1994); and, Gel Electrophoresis of Proteins: A Practical Approach, $2^{nd}$ edition Hames and Rickwood (Eds.) IRL Press, Oxford England, (1990).

Other types of separation matrices are also optionally used and discussed in U.S. patent application Ser. No. 09/093,832 filed Jun. 8, 1998, entitled "Microfluidic Matric Localizations Apparatus and Methods," by Burd Mehta and Kopf-Sill. Alternate separation matrix media include low pressure chromatography media, such as non-ionic macroreticular and macroporous resins which adsorb and release components based upon hydrophilic or hydrophobic interactions, e.g., Amberchrom and Amberlite resins (available from Supelco), Dowex, and Duolite (all available from Supelco). Other optional media include affinity media for purification and separation, such as acrylic beads, agarose beads, cellulose, sepharose, or the like. In addition, a wide variety of resins and chromatography media are also available, e.g., from Supelco, Sigma, Aldrich, or the like, for example, biotin resins, dye resins, aluminas, carbopacks, and the like. For a review of chromatography techniques and media, see, e.g., Affinity Chromatography-A Practical Approach, Dean et al., (Eds.) IRL Press, Oxford (1985); and, Chromatographic Methods, $5^{th}$ Edition, Braithwaite et al., (1996).

For example, a processed protein sample that has been desalted and denatured in SDS is optionally electrophoresed in a linear polyacrylamide gel filled channel containing SDS to separate the proteins on the basis of molecular weight of the protein subunits. A detector, such as detector 106, is optionally positioned so that it detects the proteins that are stained in the gel with a fluorescent protein stain. The retention time of the proteins as they are electrophoresed through the gel is used, e.g., with markers, to measure the molecular weight of the proteins.

Down stream of the detector, another fluid stream, such as that in elution region 108, is used to sweep the proteins away from the end of the acrylamide filled channel and also provide a low ionic strength, conductive path for electrophoresis. This down stream fluid flow is optionally hydrodynamically driven. The fluid is preferably a buffer, most preferably optimized to facilitate adsorption to the solid phase particles introduced in the next step. Such buffers include but are not limited to Towbin's Transfer Buffer and similar buffers.

III. Attachment of Separated Components to Particle Set

After separation, the separated components of the invention are optionally contacted with a component-binding moiety that is specific to a component of interest. However, before contacting with the binding moiety, the separated components are optionally bound to a particle set to assist in the identification and detection of the component of interest.

In this embodiment, the separated components are introduced into a binding buffer upon elution from, e.g., separation region 206 or separation channel 104. Buffers are typically provided that aid the binding of the various components to the particle members of the particle set. For example, a binding buffer is optionally flowed through elution region 108 to prepare the separated components for binding to a particle set. Such buffers include, but are not limited to, biological buffers that contain alcohol to enhance, e.g., the binding proteins to the particles. For example, Towbin's transfer buffer is optionally used in the binding region to aid binding of components to particles.

After introduction of the binding buffer to the separated components, the particle set is optionally introduced, e.g., from particle well 112, into the binding region or channel, such as binding channel 110. The separated components, e.g., proteins or carbohydrates, are incubated in the binding region with the particle member types that comprise the particle set. Incubation times typically range from a few seconds to a few hours. More preferably, the incubation time lasts from about 10 seconds to about 30 minutes.

During the incubation time, the separated components, e.g., proteins or carbohydrates, bind to the particle member types. The particle member types typically comprise a polymeric material, a silica material, a ceramic material, a glass material, a magnetic material, a metallic material, an organic material, or the like. For example, the particles optionally comprise polymer or ceramic beads. The typical size of the particle member types ranges from about 0.1 micron to about 50 microns or to about 100 microns. The separated components, including the component of interest adhere, attach or bind to the particles. For example, in one embodiment, proteins adsorb onto the particles. Adsorption refers to the adhesion of the components in a thin layer to the surface of the particles or beads of the invention with which they are in contact. Beads for use in adsorption of components include PVDF, nitrocellulose, and polyamides, such as nylon.

After incubation with the separated components, resulting in binding of the components to the beads or particles of the particle set, the particles, e.g., protein-coated beads, are optionally stacked in a stacking region that is proximal to a detector. For example, the particles are optionally stacked in a stacking region located at the end of detection channel 114, with a barrier, e.g., a barrier or shallow depth channel region, in the downstream end of the detection channel to prevent the beads from flowing into waste well 124. The protein coated beads or particle member types stack in the detection channel such that they pile up sequentially. This creates a linear array of protein coated beads that are arranged according to elution time, for example, the fastest eluting proteins stack first in the downstream portion of the stacking region and the slowest eluting proteins stack last in the upstream portion of the stacking region. In another embodiment, different sizes of beads are optionally used and depths and/or widths in the stacking region are optionally varied to control stacking of, e.g., a particular elution band in a particular region.

Particle stacking and the type of beads or particles available to form particle sets are described further in U.S. patent application Ser. No. 60/128,643, filed Apr. 9, 1999 by Burd Mehta et al and in U.S. Ser. No. 09/510,626 of the same title filed Feb. 22, 2000 by Burd Mehta et al. For example, in particle stacking, a first set of particles is flowed into a microfluidic region, e.g., the stacking region, having a sufficiently small dimension to inhibit movement of the first particle set. The first particle set in this case stacks against the small dimensioned region . Subsequently, a second, third, fourth . . . nth set of particles is optionally moved into the region where they will stack against the first particle set. Even though the second . . . nth particle sets are small enough to pass through the small dimensioned region of the channel, they are retained by stacking against the first particle set. Thus, the first particle set acts as a matrix preventing passage of subsequent particle sets. Therefore, the particles can be stacked according to the elution time of the component attached to them.

Once the particles, e.g., protein-coated beads, are stacked in the stacking region of the detection channel or in the detection region of the main channel or separation channel, various reagents are optionally added to contact and bind to or react with the components that are attached or adsorbed onto the particles. For example, reagents that bind to the particles that have open binding sites or to the components, e.g., proteins, that are attached to the particles are optionally added in the stacking region.

Blocking solutions are preferably added after binding the components to the particle set. The blocking solution is optionally added, e.g., from reservoir 116 into detection channel 114, after the particle stacking since the particle size is such that a solution is still free to flow among and through the particles and detection region. The blocking solution typically comprises a blocking protein. The blocking solution is preferably a buffer solution comprising casein, solubilized non-fat dry milk, gelatin or bovine serum albumin. The blocking protein will adhere, bind or adsorb to the particles or beads, thus saturating any remaining sites on the particles that have not been filled with separated components comprising the sample. The blocking solution thus prevents or blocks any non-specific binding of the component-binding moiety to the particles or beads.

The blocked particles are then sequentially treated with a component-binding moiety specific to the component of interest, and a washing solution to remove unbound component-binding moiety.

IV. Introduction of a Component-binding Moiety Specific to the Component of Interest In one embodiment, the blocked beads are treated with a component-binding moiety, e.g., an antibody or lectin, that is specific to the component of interest, e.g., a protein or carbohydrate. The component-binding moiety reacts with the components bound to the particles by binding specifically to the component of interest. For example, a lectin or an antibody, upon release from component-binding moiety well 210, contacts the eluted separated proteins in main channel 204, where binding to the component of interest, e.g., a carbohydrate or protein, typically takes place. Alternatively, a component-binding moiety is released from an antibodyenzyme conjugate well, such as reservoir 118, and then transported to the stacking region in detection channel 114, where it binds to the component of interest and is detected.

The incubation time for this binding to occur varies from a few seconds to a few hours. Preferably the binding occurs over a period that ranges from about 1 second to about 30 minutes. The time is optionally varied to adjust the sensitivity of detection.

In one embodiment, the component-binding moiety is a "protein-binding moiety" specific to a protein of interest. The protein-binding moiety is any molecule, e.g., a protein, a nucleic acid, an antibody, an enzyme, or the like, that specifically binds to a protein of interest in the present invention. The phrase "specifically binds" to a protein or component refers to a binding reaction that is determinative of the presence of the protein in a heterogeneous population of proteins and other biologics. Thus when a protein-binding moiety specific to a protein of interest binds to that protein (or when a component-binding moiety specific to a component of interest binds to the component of interest) it binds to that particular protein or component preferentially out of a complex mixture. For example, it binds at least two times the background, more typically 10 to 100 times background, and does not substantially bind in significant amounts to other proteins or components in the sample. Specific binding to a polyclonal antibody may require an antibody that is selected for its specificity for a particular protein or component as discussed below. The "protein-binding moiety" or "component-binding moiety" of the present invention is typically labeled with a detectable label as described below and then detected after binding to the "component of interest" or the "protein of interest," thus detecting the component or protein of interest.

In one typical embodiment, the "component-binding moiety" is a "protein-binding moiety," such as an antibody, receptor, or ligand. An "antibody" is a multifunctional glycoprotein produced in nature by the immune system. Antibodies function in the immune system to prevent infection by microorganisms. They perform this function by recognizing and binding to particular molecular configurations on invading microorganisms, each antibody being able to bind only one or a small number of related molecular configurations or antigens. Typically, an antibody comprises a framework from an immunoglobulin gene or fragment that specifically binds and recognizes an antigen. The recognized immunoglobulin genes include the kappa, lambda, alpha, gamma, delta, epsilon, and mu constant region genes as well as the various immunoglobulin variable genes. Light chains are classified as either kappa or lambda. Heavy chains are classified as gamma, mu, alpha, delta, or epsilon, which define the immunoglobulin classes, IgG, IgM, IgA, IgD, and IgE.

An exemplary immunoglobulin or antibody structural unit comprises a tetramer. Each tetramer is composed of two identical pairs of polypeptide chains, each pair having one light and one heavy chain. The N-terminus of each chain defines a variable region of about 100–110 or more amino acids primarily responsible for antigen recognition.

Antibodies exist as intact immunoglobulins or as a number of well-characterized fragments produced by digestion with various peptidases. While various antibody fragments are defined in terms of the digestion of an intact antibody, one of skill will recognize that such fragments may be synthesized de novo either chemically or by using recombinant DNA technology.

For preparation of monoclonal or polyclonal antibodies, any technique known in the art is optionally used. (see, e.g., Paul (ed.) (1993) *Fundamental Immunology, Third Edition* Raven Press, Ltd., New York Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256:495–497. Other suitable techniques for antibody preparation include selection of libraries of recombinant antibodies in phage or similar vectors. See, Huse et al. (1989) *Science* 246:1275–1281; and Ward et al.(1989) *Nature* 341:544–546. Specific monoclonal and polyclonal antibodies and antisera will usually bind with a KD of at least about 0.1 $\mu$M, preferably at least about 0.01 $\mu$M or better, and most typically and preferably, 0.001 $\mu$M or better.

In other embodiments, the component-binding moiety comprises biotin, avidin, a lectin, small organic molecule or the like. For example, when the component of interest is a carbohydrate, the component-binding moiety is preferably a lectin, e.g., a glycoprotein that binds oligosaccharides or carbohydrates typically through precise and/or stereospecific interactions. Another specifically binding system of interest in the present invention is the avidin-biotin system. Biotin is optionally linked to proteins or nucleic acids and used as a label. Detection of a biotinylated protein or nucleic acid occurs due to the enzymatic or chemiluminescent reaction of biotin with a detector complex comprising streptavidin or avidin, which binds tightly to the biotin. The "component-binding moiety" is a molecule or substance that binds to the component of interest.

The component-binding moiety is preferably labeled with a detectable label that allows detection of the component-binding moiety, thus also the detection of the component of interest to which it is bound. The label is optionally a fluorescent label, a chemiluminescent label, an enzyme label, or a colorimetric label.

A "label" is any composition detectable by spectroscopic, photochemical, biochemical, immunochemical, electrical, optical or chemical means. Useful labels in the present invention include fluorescent dyes (e.g., fluorescein isothiocyanate, Texas red, rhodamine, and the like), radiolabels (e.g., 3H, 125I, 35S, 14C, 32P, 33P, etc.), enzymes (e.g., horse-radish peroxidaase, alkaline phosphatase etc.), and colorimetric labels such as gold colored glass or plastic e.g., polystyrene, polypropylene, latex, etc.) beads.

The label is coupled directly or indirectly to a component of the assay according to methods well known in the art. As indicated above, a wide variety of labels are used, with the choice of label depending on the sensitivity required, ease of conjugation with the component of interest or the component-binding moiety, stability requirements, available instrumentation and disposal provisions. Non-radioactive labels are often attached by indirect means. Generally, a ligand molecule (e.g., biotin) is covalently bound to the component to be labeled. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands are optionally used. Where a ligand has a natural anti-ligand, for example, biotin, thyroxine, or cortisol, it is used in conjunction with the labeled naturally occurring anti-ligand. Alternatively, any haptogenic or antigenic compound is used in combination with an antibody (see, e.g., Coligan (1991) *Current Protocols in Immunology*, Wiley/Greene, N.Y.; and Harlow and Lane (1989) *Antibodies: A Laboratory Manual*, Cold Spring Harbor Press, N.Y. for a general discussion of how to make and use antibodies). The components of the invention are also optionally conjugated directly to signal-generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include, e.g., luciferin and 2,3,-dihydrophthalalzinediones, e.g., luminol.

For example, an antibody is preferably labeled with an enzyme or other label. The enzyme label is optionally a hydrolase such as alkaline phosphatase that is used with dioxetane substrates to generate chemiluminescence that is screened that can be scanned by the same detector used for the detection of electrophoretic mobility. Alternatively, a linear or 2-dimensional array CCD detector is used to measure the chemiluminescence. There are also fluorescent substrates for alkaline phosphatase that precipitate in situ when hydrolyzed and thereby deposit fluorescent dye where the enzyme label is present. The fluorescence is optionally detected by a fluorescence detector that is scanned along the channel.

The results from the electrophoresis and the antibody detection are optionally correlated and the molecular weight of the antibody reactive protein or proteins is determined. The graphic display of the results is optionally in the form of linear intensity plots or virtual stained gel images that are similar to standard western assay results.

In some embodiments, a component-binding moiety in a channel in which flow is electrokinetically driven is optionally derivatized with a transport functionality, e.g., an electrokinetically charged moiety, to flow in a direction opposite to that of a component of interest. For example, a mixture of proteins flowing downstream in an electrophoretic separation matrix are optionally contacted by a derivatized antibody, e.g., an acetylated antibody, flowing upstream in the separation matrix.

In other embodiments, a first and a second label are used to distinguish the component-binding moiety from the separated components and detect both concurrently. In some embodiments, the first and the second label interact when in proximity (e.g., due to fluorescence resonance energy transfer or "FRET"), and the relative proximity of the first label and the second label is determined by measuring a change in the intrinsic fluorescence of the first or second label. For example, the emission of the first label is sometimes quenched by proximity to the second label. The technique is particularly suited to measuring of binding reactions, e.g., protein-protein interactions such as a protein of interest binding to an antibody. Many appropriate interactive labels are known to those of skill in the art. For example, fluorescent labels, dyes, and antibody labels are all appropriate. Examples of interactive fluorescent label pairs include terbium chelate and TRITC (tetrarhodamine isothiocyanate), europium cryptate, allophycocyanin, and many others. Similarly, two colorimetric labels result in combinations that yield a third color, e.g., a blue emission in proximity to a yellow emission provides an observed green emission. For more information, see, e.g., *Handbook of Fluorescent Probes and Research Chemicals* published by Molecular Probes, Inc., Eugene, Oreg. (1996).

Detectors for detecting the labeled components of the invention are well known to those of skill in the art. For example, where the label is a radioactive label, a scintillation counter or autoradiography is optionally used. Where the label is a fluorescent label moiety, it is detected by exciting the fluorochrome with the appropriate wavelength of light and detecting the resulting fluorescence. This is discussed in more detail below.

Wash solutions of varying stringency are then optionally applied to the particle set to remove any unbound component-binding moieties. Stringent wash solutions are optionally applied to remove, e.g., any antibodies bound to a component in a non-specific manner. This works to reduce background levels of the labeled component-binding moiety.

The washing solutions of the present invention typically comprise BSA solutions, detergent solutions, and the like.

In another embodiment, the component-binding moiety is added to the separated components as they elute from the separation matrix. The component-binding moiety then reacts with the component of interest and specifically binds to it. The component-binding moiety is typically labeled as discussed above. In addition, the mixture of components is also optionally labeled and the two are detected concurrently. Two different labels are preferred when concurrent detection is desired. In this embodiment, the separated components are not bound to the particle set and detected by location in the stacked array of particles. In this embodiment, the component of interest is given a label and individually detected and identified by retention time. The component-binding moiety in this case has a detectably different label from the label on the separated components or component of interest.

After binding of the component-binding moiety to the component of interest, the labeled moieties, e.g., a luminescent, fluorescent, or color label on the component-binding moiety or the separated components, are detected, e.g., bound to the particle set in detection channel 114 or in detection region 216 as described below. Both the separated components and the component-binding moiety are optionally detected.

V. Detectors and Integrated Systems

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquotting, and the like. Similarly, downstream operations may include similar operations, including, e.g., separation of sample components, labeling of components, assays and detection operations, electrokinetic or pressure-based injection of components into contact with particle sets, or materials released from particle sets, or the like.

Instrumentation

In the present invention, materials such as cells, proteins, or antibodies are optionally monitored and/or detected so that presence of a component of interest can be detected or an activity can be determined. Depending on the label signal measurements, decisions are optionally made regarding subsequent fluidic operations, e.g., whether to assay a particular component in detail to determine, e.g., kinetic information.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Fluid Direction System

A variety of controlling instrumentation is optionally utilized in conjunction with the microfluidic devices described above, for controlling the transport and direction of fluidic materials and/or materials within the devices of the present invention, e.g., by pressure-based or electrokinetic control.

In the present system, the fluid direction system controls the transport, flow and/or movement of a sample through the microfluidic device. For example, the fluid direction system optionally directs the movement of the sample through the component separation region or channel, resulting in separated components. It optionally directs movement of a particle set and the separated components to a binding region, resulting in binding of the separated components to the plurality of particle member types. It also directs movement of the component-binding moiety to the binding region, resulting in binding of the component-binding moiety to the component of interest. In addition, movement of the particle set, separated components, and component-binding moiety to the detection region, where the component-binding moiety is detected, is also controlled by the fluid direction system.

For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. As noted above, the systems described herein can also utilize electrokinetic material direction and transport systems. Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467 filed Jan. 28, 1999.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

Detector

The devices herein optionally include signal detectors, e.g., which detect fluorescence, phosphorescence, radioactivity, pH, charge, absorbance, luminescence, temperature, magnetism, color, or the like. Fluorescent and chemiluminescent detection is especially preferred.

The detector(s) optionally monitors one or a plurality of signals from downstream of the binding region or channel in which a component of interest, e.g., a protein, and a component-binding moiety specific to the component of interest, e.g., an antibody are mixed so that binding occurs. For example, the detector optionally monitors an optical signal that corresponds to a labeled component, such as a labeled antibody located, e.g., in detection region 216 or detection channel 114. In another embodiment, the detector can monitor a plurality of optical signals, which correspond in position to various separated components, e.g., proteins that have been separated by weight. For example, the detector is positioned in the stacking region and monitors signals from the plurality of separated components bound to a particle set and stacked according to retention time, thus detecting the plurality of components. In another embodiment, the detector is positioned at the downstream end of the separation region or channel and detects the plurality of signals from the separated components as they elute from the separation matrix. In this embodiment, a labeled component-binding moiety is optionally added prior to detection, such that the detector monitors the plurality of signals from the separated components and the signal from the component-binding moiety as it binds to the component of interest.

Example detectors include photo multiplier tubes, a CCD array, a scanning detector, a galvo-scanner or the like. Proteins, antibodies, or other components which emit a detectable signal can be flowed past the detector, or, alternatively, the detector can move relative to the array to determine protein position (or, the detector can simultaneously monitor a number of spatial positions corresponding to channel regions, e.g., as in a CCD array). For example, when particle member types are stacked in a detection region, the detector can move relative to the stacked particles and detect them according to position within the stack.

The detector can include or be operably linked to a computer, e.g., which has software for converting detector signal information into assay result information, e.g., molecular weight based on retention time or elution time, identity of a protein, or the like.

Signals from arrays are optionally calibrated, e.g., by calibrating the microfluidic system by monitoring a signal from a known source.

A microfluidic system can also employ multiple different detection systems for monitoring the output of the system. Detection systems of the present invention are used to detect and monitor the materials in a particular channel region (or other detection region). Once detected, the flow rate and velocity of cells in the channels is also optionally measured and controlled as described above.

Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "proximal," to a particular element or region, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials such as labeled cells, the detector typically includes a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources are required for other detection systems. For example, broad band light sources are typically used in light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the fluid direction system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. For example, the software optionally directs the fluid direction system to transport the separated components to the binding channel, the particle set to the binding channel, the component-binding moiety to the stacking region, the particle set to the stacking region, and any other movement necessary to detect the component of interest.

The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of materials in the channels. Additionally the software is optionally used to control electrokinetic or pressure-modulated injection or withdrawal of material. The injection or withdrawal is used to modulate the flow rate as described above.

In addition, the computer optionally includes software for deconvolution of the signal or signals from the detection system. For example, the deconvolution distinguishes between two detectably different spectral characteristics that were both detected, e.g., in a two-color detection system when the component-binding moiety and the separated components are both labeled.

Example Integrated System

FIG. 3, Panels A, B, and C and FIG. 4 provide additional details regarding example integrated systems that are optionally used to practice the methods herein. As shown, body structure 302 has main channel 304 disposed therein. A sample or mixture of components is optionally flowed from pipettor channel 320 towards reservoir 314, e.g., by applying a vacuum at reservoir 314 (or another point in the system) or by applying appropriate voltage gradients. Alternatively, a vacuum is applied at reservoirs 306, 308, 312 or through pipettor channel 320. Additional materials, such as buffer solutions, particle sets, washing solutions, and the like, as described above, are optionally flowed from wells 310 or 312 and into main channel 304. Flow from these wells is optionally performed by modulating fluid pressure, or by electrokinetic approaches as described (or both). The arrangement of channels depicted in FIG. 3 is only one possible arrangement out of many which are appropriate and available for use in the present invention. Alternatives are provided in FIG. 1 and FIG. 2.

Samples and materials are optionally flowed from the enumerated wells or from a source external to the body structure. As depicted, the integrated system optionally includes pipettor channel 320, e.g., protruding from body 302, for accessing a source of materials external to the microfluidic system. Typically, the external source is a microtiter dish or other convenient storage medium. For example, as depicted in FIG. 4, pipettor channel 320 can access microwell plate 408, which includes sample materials, component-binding moieties, wash solutions, blocking solutions, and the like, in the wells of the plate.

Detector 406 is in sensory communication with channel 304, detecting signals resulting, e.g., from labeled component-binding moieties attached to the component of interest. Detector 406 is optionally coupled to any of the channels or regions of the device where detection is desired. Detector 406 is operably linked to computer 404, which digitizes, stores, and manipulates signal information detected by detector 406, e.g., using any of the instructions described above, e.g., or any other instruction set, e.g., for determining retention time, molecular weight or identity.

Fluid direction system 402 controls voltage, pressure, or both, e.g., at the wells of the systems or through the channels of the system, or at vacuum couplings fluidly coupled to channel 304 or other channel described above. Optionally, as depicted, computer 404 controls fluid direction system 402. In one set of embodiments, computer 404 uses signal information to select further parameters for the microfluidic system. For example, upon detecting the presence of a component of interest in a sample from microwell plate 408, the computer optionally directs addition of a potential modulator of the component of the interest into the system.

Kits

Generally, the microfluidic devices described herein are optionally packaged to include reagents for performing the device's preferred function. For example, the kits can include any of microfluidic devices described along with assay components, reagents, sample materials, proteins, antibodies, particle sets, control materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

Kits also optionally include packaging materials or containers for holding microfluidic device, system or reagent elements.

The discussion above is generally applicable to the aspects and embodiments of the invention described in the claims.

Moreover, modifications can be made to the method and apparatus described herein without departing from the spirit and scope of the invention as claimed, and the invention can be put to a number of different uses including the following:

The use of a microfluidic system for performing the western blot type assays as set forth herein.

The use of a microfluidic system for detecting a component of interest by attaching the component of interest to a particle set as described herein.

The use of a microfluidic system for detecting a protein by attaching the protein to a particle as described herein.

The use of a microfluidic system for detecting a protein by attaching the protein to a particle and then binding an antibody to the protein and detecting the antibody as described herein.

The use of a microfluidic system as described herein for separation of a component mixture and detection of a component of interest.

The use of a microfluidic system or device as described herein to detect a component of interest.

The use of a microfluidic system or device as described herein to detect a protein of interest.

The use of a microfluidic system or device as described herein to detect a carbohydrate of interest.

An assay utilizing a use of any one of the microfluidic systems or substrates described herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patent applications, patents, and other documents cited in this application are incorporated by reference in their entirety for all purposes to the same extent as if each individual publication or patent document were individually so denoted.

What is claimed is:

1. A method for detecting at least one component of interest in a mixture of components in a microfluidic system, the method comprising the steps of:
   (i) flowing the mixture of components, which mixture of components comprises the at least one component of interest, through a separation channel region in a first microfluidic channel, resulting in one or more separated components, each of the one or more separated components bearing a first detectable label;
   (ii) detecting the first detectable label associated with the one or more separated components in a first detection channel region located downstream of the separation channel region to determine a physical property of the one or more separated components based on the retention time of the one or more separated components through the separation channel region;

(iii) contacting the one or more separated components with a component binding moiety bearing a second detectable label in the first or a second microfluidic channel in a channel region located downstream from the first detection channel region, thereby binding at least a portion of the at least one component of interest to the component-binding moiety;

(iv) detecting at least the second detectable labels in a second detection channel region of the first or the second microfluidic channel to thereby provide a detection signal corresponding to the at least one component of interest; and (v) deconvoluting the detection signal to identify the component of interest.

2. The method of claim 1, wherein the at least one component of interest comprises a protein and the component-binding moiety comprises a protein-binding moiety.

3. The method of claim 1, wherein the component-binding moiety comprises an antibody specific to the at least one component of interest.

4. The method of claim 1, wherein the at least one component of interest comprises a carbohydrate and the component-binding moiety comprises a carbohydrate-binding moiety.

5. The method of claim 4, wherein the carbohydrate-binding moiety comprises a lectin specific to the carbohydrate.

6. The method of claim 1, wherein the one or more separated components are bound to or adsorbed to one or more particle set in a binding channel region located downstream of the first detection channel region.

7. The method of claim 6, wherein the one or more particle set comprises a polymeric material, a silica material, a ceramic material, a glass material, a magnetic material, a metallic material, or an organic material.

8. The method of claim 6, wherein the one or more particle set comprise a material selected from the group consisting of: PVDF, polyamide, nylon, and nitrocellulose.

9. The method of claim 7, wherein particles in the particle set are from about 0.1 mm to about 50 mm in diameter.

10. The method of claim 6, wherein the one or more particle set comprises the component-binding moiety.

11. The method of claim 1, wherein contacting the one or more separated components with a component binding moiety comprises flowing the component binding moiety into the first or second microchannel through a side channel fluidly coupled thereto by applying pressure to a fluid containing the component binding moiety.

12. The method of claim 1, comprising electrokinetically flowing the mixture of components through the separation channel region.

13. The method of claim 1, comprising electrophoretically separating the mixture of components in a polymer or gel, which polymer or gel is disposed within the separation channel region.

14. The method of claim 1, wherein detecting the first and the at least second detectable labels comprises optically detecting a luminescent, color, or fluorescent label moiety fixed to each of the one or more separated components and the at least one component binding moiety.

15. The method of claim 1, wherein the first and second detectable labels comprise detectably different fluorescent label moieties, and detecting the first and the at least second detectable labels comprises detecting the detectably different fluorescent label moieties.

16. The method of claim 1, wherein detecting the first detectable label produces a first data set and detecting the at least second detectable label produces a second data set.

17. The method of claim 16, further comprising superimposing the first data set and the second data set to identify the at least one component of interest.

18. The method of claim 1, wherein the first detectable label and the second detectable label comprise detectably different spectral characteristics.

19. The method of claim 18, wherein the detectably different spectral characteristics differ by one or more of a different excitation or emission maximum.

20. The method of claim 1, wherein the first detectable label comprises a fluorescent moiety and the second detectable label comprises a chemiluminescent moiety.

21. The method of claim 1, wherein the first detectable label comprises a first fluorescent dye and the second detectable label comprises a second fluorescent dye.

22. The method of claim 21, wherein the first fluorescent dye and the second fluorescent dye comprise detectably different spectral characteristics.

23. The method of claim 22, wherein the detectably different spectral characteristics differ by one or more of a different excitation or emission maxim.

24. The method of claim 1, wherein the first detectable label comprises a first colorimetric label and the second detectable label comprises a second calorimetric label.

25. The method of claim 24, wherein the first calorimetric label and the second colorimetric label comprise detectably different spectral characteristics.

26. The method of claim 6, wherein the binding channel region and the second detection channel region are both located in the second microchannel.

27. The method of claim 1, wherein the deconvoluting the detection signal to identify the at least one component of interest is done to perform a western style assay.

28. The method of claim 6, further comprising stacking the one or more particle set in a stacking channel region corresponding to the second detection channel region such that the particles in the one or more particle set stack proximal to one another sequentially.

29. The method of claim 28, wherein contacting the one or more separated components with a component binding moiety comprises flowing the component binding moiety into the stacking channel region.

30. The method of claim 29, wherein detecting the at least second detectable label comprises scanning the second detection channel region along a length of the second detection channel region with a fluorescence detector.

31. The method of claim 28, wherein the binding channel region and the stacking channel region are both located in the second microchannel.

32. The method of claim 1, wherein the physical property is the molecular weight of the one or more separated components.

* * * * *

UNITED STATES PATENT AND TRADEMARK OFFICE
CERTIFICATE OF CORRECTION

PATENT NO. : 6,613,581 B1
DATED : September 2, 2003
INVENTOR(S) : H. Garrett Wada et al.

It is certified that error appears in the above-identified patent and that said Letters Patent is hereby corrected as shown below:

<u>Column 27,</u>
Line 8, please delete "labels" and insert -- label --.

<u>Column 28,</u>
Lines 31 and 32, please delete "calorimetric" and insert -- colorimetric --.

Signed and Sealed this

Eleventh Day of November, 2003

JAMES E. ROGAN
*Director of the United States Patent and Trademark Office*